US010073522B2

(12) United States Patent
Kowalewski et al.

(10) Patent No.: US 10,073,522 B2
(45) Date of Patent: Sep. 11, 2018

(54) ARTICLES OF HANDWEAR FOR SENSING FORCES APPLIED TO MEDICAL DEVICES

(71) Applicant: Regents of the University of Minnesota, Minneapolis, MN (US)

(72) Inventors: Timothy M. Kowalewski, Saint Paul, MN (US); Sachin Bijadi, Bengaluru (IN); Darrin D. Beekman, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 275 days.

(21) Appl. No.: 14/569,380

(22) Filed: Dec. 12, 2014

(65) Prior Publication Data

US 2016/0169754 A1    Jun. 16, 2016

(51) Int. Cl.
*G01L 1/18*  (2006.01)
*G01L 5/00*  (2006.01)
(Continued)

(52) U.S. Cl.
CPC .............. *G06F 3/014* (2013.01); *A61B 42/10* (2016.02); *G01L 5/162* (2013.01); *G01L 5/228* (2013.01); *A61B 2034/741* (2016.02)

(58) Field of Classification Search
CPC ....... A61B 5/11; A61B 5/6826; A61B 5/6838; A61B 2562/0247; A61B 5/6847; A61B 5/4381; A61B 5/0051; A61B 2562/046; A61B 5/14551; A61B 5/021; A61B 8/04; A61B 8/462; A61B 8/56; A61B 5/02416; A61B 8/488; A61B 5/0205; A61B 8/02; A61B 5/742; A61B 5/746; G09B 23/288; A61H 2201/5061; A61H 2201/5084; A61H 31/005; A61H 2201/5069; A61H 2201/5064; A63B 69/32; A63B 69/004; A63B 71/145; A63B 2208/12; A63B 2220/803; A63B 2230/50; A63B 71/06; A63B 71/1225; A63B 2244/102; A63B 2220/53; A63B 2225/50; A63B 2071/065; G06F 3/00
(Continued)

(56) References Cited

U.S. PATENT DOCUMENTS 4,221,273 A   9/1980  Finden
4,471,777 A   9/1984  McCorkle, Jr.
(Continued)

OTHER PUBLICATIONS

Beccai, Lucia et al. "Design and fabrication of a hybrid silicon three-axial force sensor for biomechanical applications." Sensors and Actuators A 120. 2005. pp. 370-382.
(Continued)

*Primary Examiner* — Harshad R Patel
*Assistant Examiner* — Brandi Hopkins

(57) ABSTRACT

An article of handwear for grasping a medical device in a medical environment includes a base adapted to be worn by a hand of a wearer. A sensor assembly is carried by the base. The sensor assembly is adapted to sense a force applied by the hand of the wearer, via the article of handwear, to the medical device. The sensor assembly is adapted to provide information regarding at least one shear component of the forces sensed by the sensor assembly.

19 Claims, 4 Drawing Sheets

(51) Int. Cl.
*G06F 3/01* (2006.01)
*G01L 5/22* (2006.01)
*G01L 5/16* (2006.01)
*A61B 42/10* (2016.01)
*A61B 34/00* (2016.01)

(58) Field of Classification Search
USPC ............ 601/41; 73/12.09, 862.046, 862.541; 600/587
See application file for complete search history.

(56) References Cited

U.S. PATENT DOCUMENTS

| | | | |
|---|---|---|---|
| 4,576,162 A | 3/1986 | McCorkle | |
| 4,582,056 A | 4/1986 | McCorkle et al. | |
| 4,943,289 A | 7/1990 | Goode et al. | |
| 4,988,347 A | 1/1991 | Goode et al. | |
| 5,011,482 A | 4/1991 | Goode et al. | |
| 5,012,680 A | 5/1991 | Castagnoli | |
| 5,013,310 A | 5/1991 | Goode et al. | |
| 5,199,401 A | 4/1993 | O'Neil et al. | |
| 5,207,683 A | 5/1993 | Goode et al. | |
| 5,442,729 A * | 8/1995 | Kramer ................ | A61B 5/6806 128/925 |
| 5,494,045 A | 2/1996 | Kiviranta et al. | |
| 5,507,751 A | 4/1996 | Goode et al. | |
| 5,632,749 A | 5/1997 | Goode et al. | |
| 5,651,781 A | 7/1997 | Grace | |
| 5,788,659 A | 8/1998 | Haas | |
| 6,370,971 B1 | 4/2002 | Olson | |
| 7,014,642 B1 | 3/2006 | Perone | |
| 7,072,703 B2 | 7/2006 | Zhang et al. | |
| 7,627,380 B2 | 12/2009 | Podhajsky et al. | |
| 7,762,449 B2 | 7/2010 | Cheng et al. | |
| 8,004,229 B2 | 8/2011 | Nowlin et al. | |
| 2002/0166379 A1 | 11/2002 | Paros et al. | |
| 2003/0172739 A1 | 9/2003 | Horiuchi et al. | |
| 2006/0248478 A1 * | 11/2006 | Liau ........................ | G06F 3/014 715/863 |
| 2007/0186665 A1 * | 8/2007 | Hierold ................ | B81B 3/0021 73/779 |
| 2009/0234367 A1 | 9/2009 | Verma | |
| 2013/0082970 A1 * | 4/2013 | Frey ........................ | G06F 3/0414 345/173 |
| 2014/0052026 A1 * | 2/2014 | Bishara ................ | A61B 5/0053 600/587 |

OTHER PUBLICATIONS

Maréchal, L. et al. "Measurement System for Gesture Characterization During Chest Physiotherapy Act on Newborn Babies Suffering from Bronchiolitis." Proceedings of the 29th Annual International Conference of the IEEE EMBS, Cité Internationale, Lyon, France. Aug. 23-26, 2007. pp. 5770-5773.

Missinne, Jeroen et al. "Embedded Flexible Optical Shear Sensor." IEEE Sensors 2010 Conference. 2010. pp. 987-990.

Nikonovas, A. et al. "The application of force-sensing resistor sensors formeasuring forces developed by the human hand." Proceedings of the Institution of Mechanical Engineers Part H: Journal of Engineering in Medicine, vol. 218. 2004. pp. 121-126.

Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.

\* cited by examiner

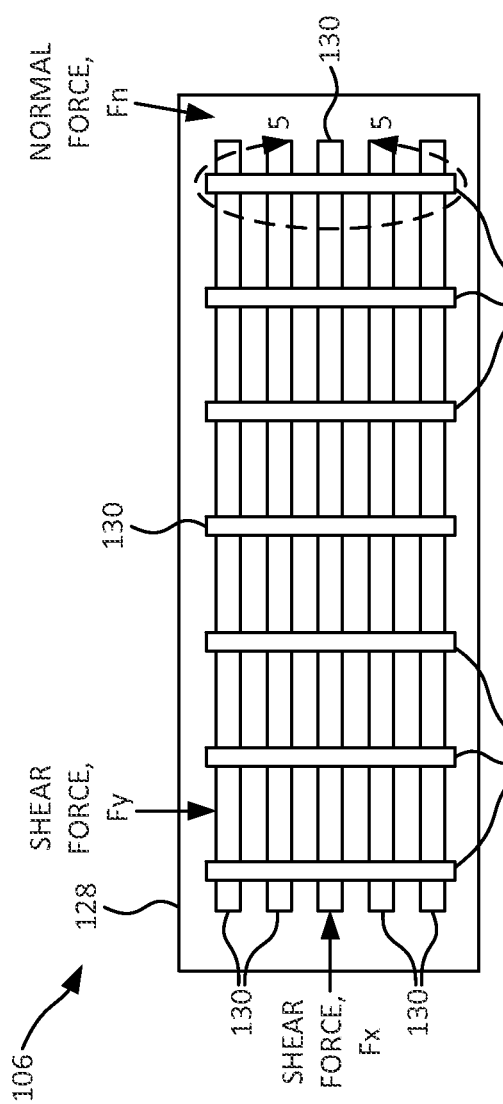
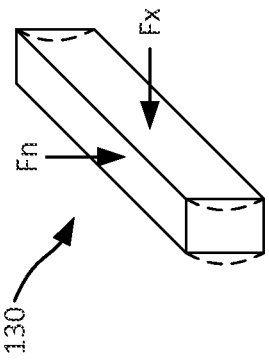

ARTICLES OF HANDWEAR FOR SENSING FORCES APPLIED TO MEDICAL DEVICES

FIELD

The present disclosure relates generally to articles of handwear that include one or more force sensors, and, more particularly, to articles of handwear for sensing normal and shear forces applied to medical devices.

BACKGROUND

Surgically implanted cardiac pacing systems, such as pacemakers and defibrillators, play an important role in the treatment of heart disease. In the 50 years since the first pacemaker was implanted, technology has improved dramatically, and these systems have saved or improved the quality of countless lives. Pacemakers treat slow heart rhythms by increasing the heart rate or by coordinating the heart's contraction for some heart failure patients. Implantable cardioverter-defibrillators stop dangerous rapid heart rhythms by delivering an electric shock.

Cardiac pacing systems typically include a timing device and a lead, which are placed inside the body of a patient. One part of the system is the pulse generator containing electric circuits and a battery, usually placed under the skin on the chest wall beneath the collarbone. To replace the battery, the pulse generator must be changed by a simple surgical procedure every 5 to 10 years. Another part of the system includes the wires, or leads, which run between the pulse generator and the heart. In a pacemaker, these leads allow the device to increase the heart rate by delivering small timed bursts of electric energy to make the heart beat faster. In a defibrillator, the lead has special coils to allow the device to deliver a high-energy shock and convert potentially dangerous rapid rhythms (ventricular tachycardia or fibrillation) back to a normal rhythm. Additionally, the leads may transmit information about the heart's electrical activity to the pacemaker.

For both of these functions, leads must be in contact with heart tissue. Most leads pass through a vein under the collarbone that connects to the right side of the heart (right atrium and right ventricle). In some cases, a lead is inserted through a vein and guided into a heart chamber where it is attached with the heart. In other instances, a lead is attached to the outside of the heart. To remain attached to the heart muscle, most leads have a fixation mechanism, such as a small screw and/or hooks at the end.

Within a relatively short time after a lead is implanted into the body, the body's natural healing process forms scar tissue along the lead and possibly at its tip, thereby fastening it even more securely in the patient's body. Leads usually last longer than device batteries, so leads are simply reconnected to each new pulse generator (battery) at the time of replacement. Although leads are designed to be implanted permanently in the body, occasionally these leads must be removed, or extracted. Leads may be removed from patients for numerous reasons, including infections, lead age, and lead malfunction.

Removal or extraction of the lead may be difficult. As mentioned above, the body's natural healing process forms scar tissue over and along the lead, and possibly at its tip, thereby encasing at least a portion of the lead and fastening it even more securely in the patient's body. In addition, the lead and/or tissue may become attached to the vasculature wall. Both results may, therefore, increase the difficulty of removing the leads from the patient's vasculature.

A variety of tools have been developed to make lead extraction safer and more successful. Current lead extraction techniques include mechanical traction, mechanical devices, and laser devices. Mechanical traction may be accomplished by inserting a locking stylet into the hollow portion of the lead and then pulling the lead to remove it. An example of such a locking stylet is described and illustrated in U.S. Pat. No. 6,167,315 to Coe et al., which is hereby incorporated herein by reference in its entirety for all that it teaches and for all purposes.

Monitoring traction forces (i.e., shear forces) applied by a medical practitioner to a mechanical traction device would facilitate monitoring lead extraction procedures and evaluating practitioner skill during training simulations. However, devices for measuring forces applied by practitioners to medical devices are often invasive and can interfere with the typical workflow of a procedures. Moreover, they are typically only capable of measuring normal forces (i.e., compression or gripping forces).

SUMMARY

These and other needs are addressed by the various aspects, embodiments, and configurations of the present disclosure.

According to one embodiment of the present disclosure, an article of handwear for grasping a medical device in a medical environment includes a base adapted to be worn by a hand of a wearer; a sensor assembly carried by the base, the sensor assembly adapted to sense a force applied by the hand of the wearer, via the article of handwear, to the medical device, and the sensor assembly adapted to provide information regarding at least one shear component of the forces sensed by the sensor assembly. In some embodiments, the sensor assembly is adapted to provide information regarding one or more normal force components sensed by the sensor assembly.

According to another embodiment of the present disclosure, an article of handwear for grasping a medical device in a medical environment includes a glove adapted to be worn by a hand of a wearer; a plurality of force sensors carried by the glove, each of the plurality of force sensors adapted to sense a force applied by the hand of the wearer, via the article of handwear, to the medical device, each of the plurality of force sensors adapted to send a signal indicative of the force, and each of the plurality of force sensors including a substrate of carbon-nanotube-doped elastomer, such as PDMS, adapted to sense the force; and a plurality of elongated carbon nanotube elastomer members carried by the substrate of carbon-nanotube-doped elastomer, the plurality of elongated carbon nanotube elastomer members adapted to sense the force.

According to yet another embodiment of the present disclosure, a system for determining forces transmitted from a hand of a medical practitioner to a medical device in a medical environment includes a glove adapted to be worn by a hand of a wearer; a plurality of force sensors carried by the glove, each of the plurality of force sensors adapted to sense a force applied by the hand of the wearer, via the glove, to the medical device, each of the plurality of force sensors including: a substrate of carbon-nanotube-doped elastomer adapted to sense a normal component of the force applied to the medical device; a grid of elongated carbon nanotube members carried by the substrate of carbon-nanotube-doped elastomer, the grid of elongated carbon nanotube members adapted to sense a total force of the force applied to the medical device; and a processor in operable communication with the plurality of force sensors, the processor adapted to determine a shear component of the force applied to the medical device by subtracting the normal component from the total force.

These and other advantages will be apparent from the disclosure of the aspects, embodiments, and configurations contained herein.

As used herein, "carbon nanotube member" refers to any suitable elastomer doped with particles to provide a piezo-resistive effect, such as, for example, carbon nanotubes, graphene flakes, graphite flakes, silver nanoparticles, or other means of inducing piezo-resistivity in a stretchable media like an elastomer.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The terms "analyze", "determine", "calculate" and "compute", and variations thereof, as used herein, are used interchangeably and include any type of methodology, process, mathematical operation or technique.

The term "medical environment" includes environments in which one or more medical practitioners (e.g., surgeons) conduct a medical procedure on a subject (e.g., a human patient) or training environments that simulate medical procedures.

The term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4 is a top view of a force sensor of the sensor assembly of FIG. 3; and

FIG. 5 is a detail perspective view of an elongated element of the force sensor within line 5-5 of FIG. 4.

DETAILED DESCRIPTION

Figure 1:
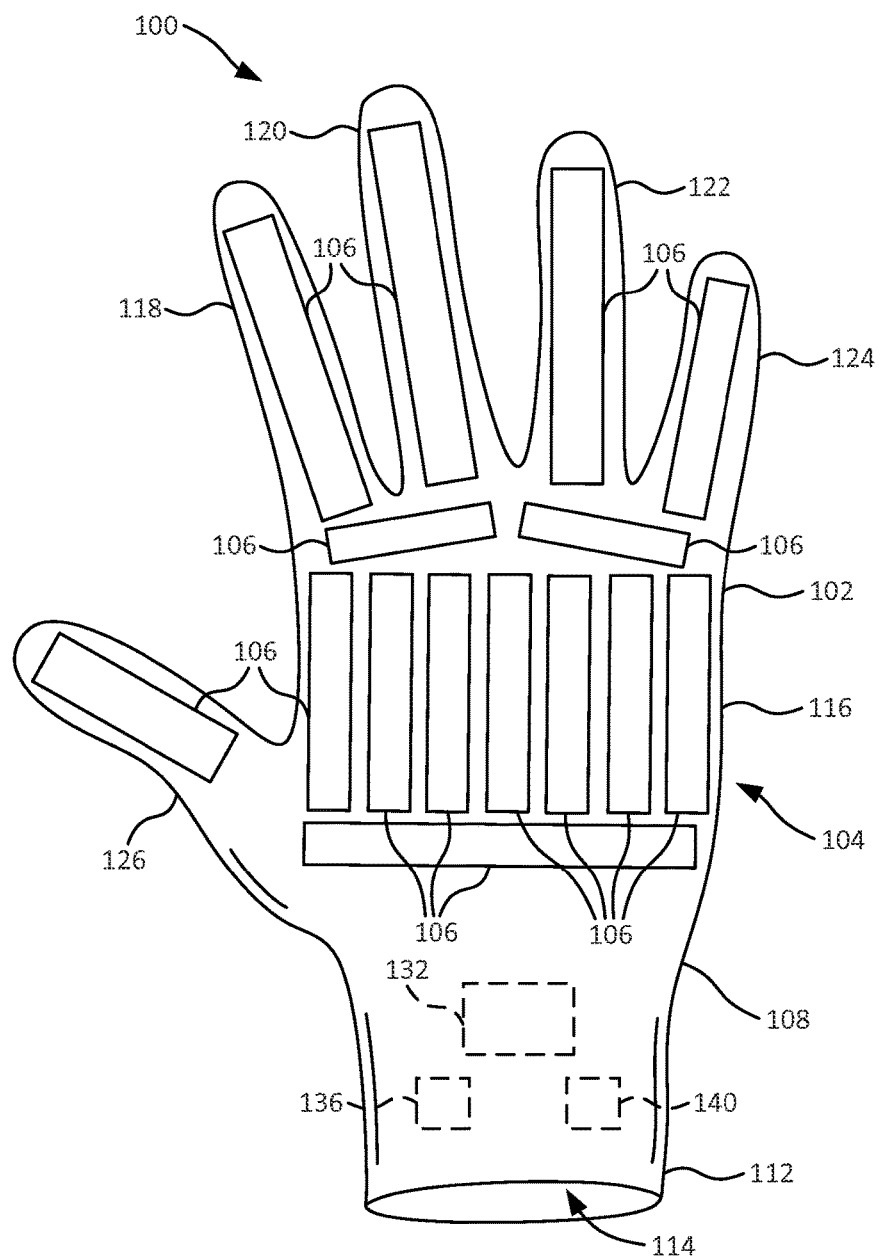
FIG. 1 is a palmar view of an embodiment of an article of handwear for sensing normal and shear forces applied to medical devices.
Figure 2:
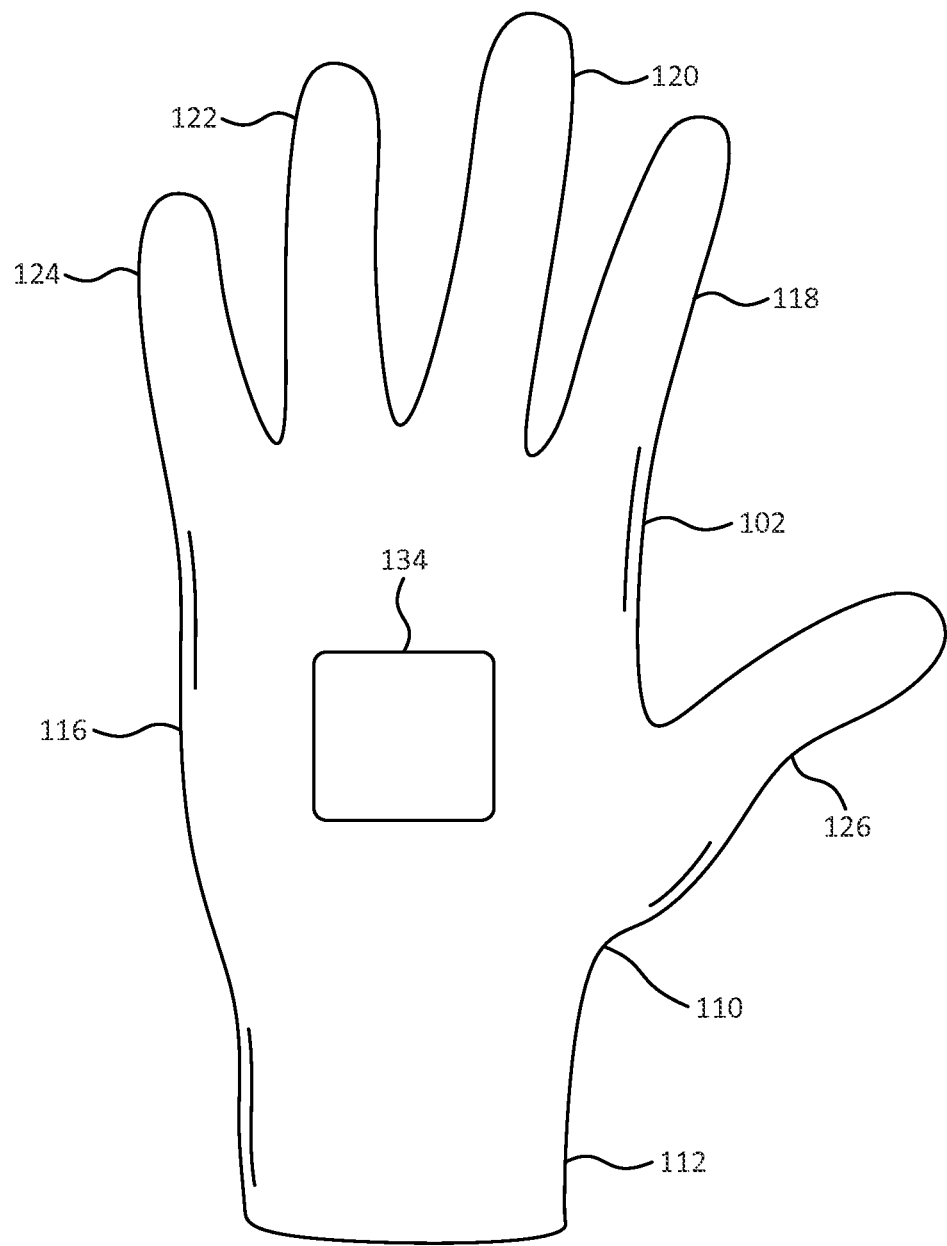
FIG. 2 is a dorsal view of the article of handwear of FIG. 1.

Referring to FIGS. 1 and 2, an embodiment of an article of handwear 100 is illustrated. FIG. 1 is a palmar view of the article of handwear 100, and FIG. 2 is a dorsal view of the article of handwear 100. The article of handwear 100 may be used for grasping a medical device (e.g., a locking stylet for lead extraction, such as the Lead Locking Device (LLD®) available from the Spectranetics Corporation) in a medical environment (e.g., an operating room environment or a training environment that simulates medical procedures). Generally, the article of handwear 100 includes a base 102 that carries a sensor assembly 104. The sensor assembly 104 includes one or more force sensors 106, or an array of force sensors 106, that are adapted to sense normal forces and shear forces applied by the hand of a wearer (e.g., a medical practitioner), via the article of handwear 100, to the medical device. Information regarding normal forces and shear forces can be used to monitor medical procedures (e.g., lead extraction procedures) and evaluate practitioner skill during training simulations. The aspects and advantages are described in further detail below.

The article of handwear 100 is adapted to be worn by the left hand of a wearer. However, it is to be understood that an article of handwear according to embodiments of the present disclosure could alternatively be adapted to be worn by the right hand of a wearer. One or both of the left and right articles of handwear could be worn in a medical environment and used to grasp a medical instrument.

Still referring to FIGS. 1 and 2, in some embodiments and as illustrated in the figures, the base 102 is formed as a glove that is adapted to be worn on the hand of the wearer. The glove may be formed of various flexible materials, such as one or more layers of fabrics, flexible polymers, and the like. Alternatively, the base 102 may take other forms. For example, the base 102 may include a frame having a plurality of interconnected, flexible struts (not shown).

In some embodiments, the base 102 includes a palmar side 108 and a dorsal side 110. As the names imply, the palmar side 108 is adapted to engage the palmar side of the hand of the wearer, and the dorsal side 110 is adapted to engage the dorsal side of the hand of the wearer. In some embodiments, the palmar side 108 and the dorsal side 110 together define one or more of the following: (1) a wrist portion 112 that defines an opening 114 for receiving the hand of the wearer; (2) a palm/opisthenar portion 116 that is adapted to receive the palm and opisthenar area of the hand of the wearer; (3) a first or "index" finger portion 118 that is adapted to receive the index finger of the hand of the wearer; (4) a second or "middle" finger portion 120 that is adapted to receive the middle finger of the hand of the wearer; (5) a third or "ring" finger portion 122 that is adapted to receive the ring finger of the hand of the wearer; (6) a fourth or "small" finger portion 124 that is adapted to receive the small finger of the hand of the wearer; and (7) a fifth or "thumb" portion 126 that is adapted to receive the thumb of the hand of the wearer.

Figure 3:
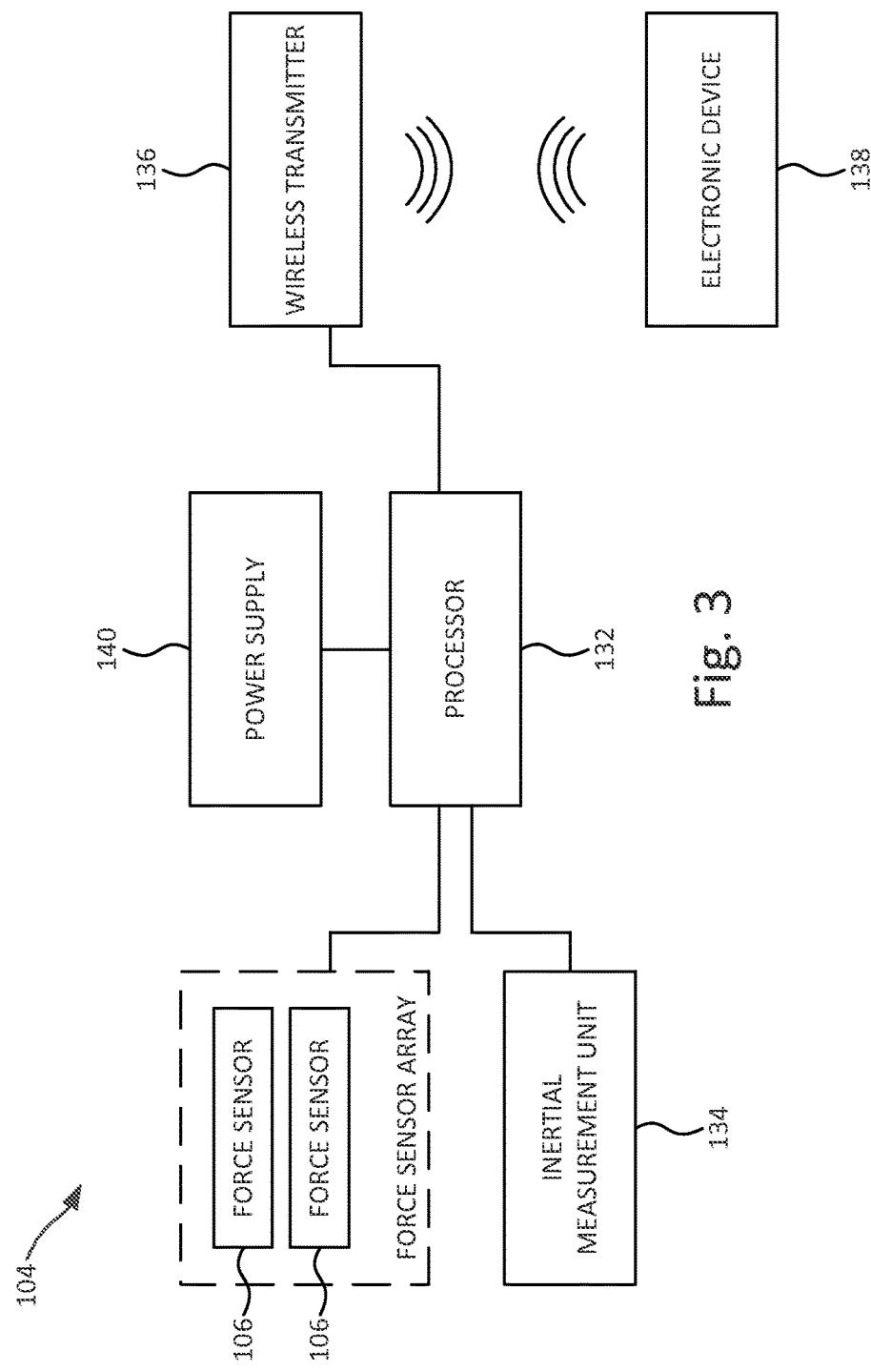
FIG. 3 is a schematic illustration of a sensor assembly of the article of handwear of FIG. 1 and an electronic device in operable communication with the sensor assembly.

Referring to FIGS. 1 and 3, the sensor assembly 104 includes the force sensors 106 that are adapted to sense normal forces and shear forces applied by the hand of a wearer, via the article of handwear 100, to the medical device. In some embodiments, the force sensors 106 are carried on the palmar side 108 of the article of handwear 100. In some embodiments, one or more force sensors 106 may be carried by any of the palm/opisthenar portion 116, the first finger portion 118, the second finger portion 120, the third finger portion 122, the fourth finger portion 124, and the fifth portion 126. In some embodiments, one or more of the finger portions 118, 120, 122, 124 and the fifth portion 126 includes a force sensor 106 that extends longitudinally along the portion. In some embodiments, one or more force sensors 106 extend longitudinally and are disposed in a parallel arrangement on the palm/opisthenar portion 116. In some embodiments, one or more force sensors 106 extend transversely on the palm/opisthenar portion 116. In some embodiments, one or more force sensors 106 extend diagonally on the palm/opisthenar portion 116. In some embodiments, one or more force sensors 106 are disposed on the knuckles of the palm/opisthenar portion 116.

Referring now to FIGS. 4 and 5, in some embodiments one or more force sensors 106 are carbon nanotube-based force sensors. In some embodiments, one or more force sensors 106 include a carbon nanotube film or substrate 128 that carries a plurality of elongated carbon nanotube members 130. In some embodiments, one or more of the elongated carbon nanotube members 130 extends longitudinally (that is, in the elongated direction of the carbon nanotube substrate 128; e.g., five nanotube members 130) and/or one or more of the elongated carbon nanotube members 130 extends transversely (that is, perpendicularly relative to the elongated direction of the carbon nanotube substrate 128; e.g., seven nanotube members 130). That is, in some embodiments the elongated carbon nanotube members 130 may be arranged in a grid. In some embodiments, the carbon nanotube substrate 128 and the elongated carbon nanotube members 130 may be printed on the base 102.

In some embodiments, the carbon nanotube-based force sensors 106 act as resonators or piezo-resistive elements when subjected to strain resulting from external forces. This strain can be either axial or radial strain. As a result, the carbon nanotube-based force sensors 106 are capable of measuring both normal forces and shear forces. That is, the carbon nanotube substrate 128 is capable of sensing the normal component $F_n$ of a force applied to the sensor 106. The normal component $F_n$ induces symmetrically distributed stresses on the substrate 128. In addition, the elongated carbon nanotube members 130 are capable of sensing the normal component $F_n$ and the shear components $F_x$ and $F_y$ of a force applied to the sensor 106. The shear components $F_x$ and $F_y$ induce stresses in the elongated carbon nanotube members 130 along their direction of application. The normal component $F_n$ sensed by the carbon nanotube substrate 128 may be subtracted from the total force sensed by the elongated carbon nanotube members 130 to obtain the shear components $F_x$ and $F_y$. Furthermore, the overall shear forces may be determined by considering the information received each of the carbon nanotube-based force sensors 106.

Each force sensor 106 is adapted to send signals indicative of sensed normal forces and shear forces. For example, the signals may include information regarding the total force and the normal component $F_n$ sensed by the force sensor 106. This information may be used, as described above, to obtain one or both of the shear components $F_x$ and $F_y$ sensed by the force sensor 106.

In some embodiments, the force sensors 106 may 'coat' the surface of the base 102 and a) have similar elastic properties to the base 102, and b) be a thin, flexible, stretchable, and relatively low-weight layer. As a result, the wearer may not feel the difference between the article of handwear 100 and a typical surgical glove. Sensors that can exhibit these properties include, for example, piezo-resistive elastomers, such as carbon nanotube-doped polydimethylsiloxane or latex doped with approximately 10 to 16 percent weight carbon nanotube doping. Other examples include similar elastomers and dopings with silver nanoparticles, graphite, carbon black, graphene, carbon fiber, or other suitable dopant.

In some embodiments, the carbon nanotube-based force sensors 106 facilitate flexibility and functionality of the article of handwear 100. That is, for other instrumented articles of handwear, bending of the sensors during hand flexing causes undesired fluctuations in force measurements.

Referring again to FIGS. 1 and 3, in some embodiments the sensor assembly 104 further includes a processor 132. The processor 132 provides suitable signal conditioning for reading sensor values (for example, the processor may include one or more differential amplifiers, filters, and analog-to-digital converters). The processor 132 may also include elements such as an application specific integrated circuit (ASIC), a state machine, a field programmable gate array (FPGA), a digital signal processor (DSP), or the like.

The processor 132 is in operable communication with the force sensors 106. In some embodiments, the processor 132 receives the signals from the force sensors 106 (e.g., signals including information regarding the total force and the normal component $F_n$ sensed by the force sensors 106). In some embodiments, the processor 132 uses the force signals to obtain one or both of the shear components $F_x$ and $F_y$ sensed by the force sensors 106, as described above. The processor 132 may determine averages of one or more of the shear components $F_x$ and $F_y$ sensed by a plurality of force sensors 106 located at different positions on the base 102.

Alternatively, the sensor assembly 104 may lack a processor, and the force sensors 106 could instead send force signals to one or more remote electronic devices, such as desktop computers, notebook computers, electronic tablets, cellular telephones, or the like. Processors of the electronic devices could use the force signals to obtain one or both of the shear components $F_x$ and $F_y$ sensed by the force sensors 106, as described above. In this case, the article of handwear 100 and the electronic devices together form a system for determining forces transmitted from the hand of the wearer to a medical device. As another alternative, each force sensor 106 may include a processor that obtains one or both of the shear components $F_x$ and $F_y$ sensed by the force sensors 106, as described above.

Referring now to FIGS. 2 and 3, in some embodiments the sensor assembly 104 further includes an inertial measurement unit (IMU) 134. In some embodiments, the IMU 134 is carried on the dorsal side 110 of the base 102. In some embodiments, the IMU 134 includes one or more accelerometers (not shown), gyroscopes (not shown), or the like to determine a spatial position and/or the motion (e.g., velocity and acceleration) of the article of handwear 100. This information may be used together with the force information described above to monitor medical procedures and evaluate practitioner skill during training simulations. The IMU 134 is adapted to send position signals and/or motion signals indicative of the spatial position and/or motion of the article of handwear 100. In some embodiments, the IMU 134 is in operable communication with the processor 132 and sends the position signals and/or motion signals to the processor 132.

Returning to FIGS. 1 and 3, in some embodiments the sensor assembly 104 further includes a wireless transmitter 136 (e.g., an antenna). The wireless transmitter 136 is in operable communication with the processor 132 and receives force, position, and/or motion information from the processor 132. The wireless transmitter 136 may transmit the force, position, and/or motion information to one or more electronic devices 138, such as desktop computers, notebook computers, electronic tablets, cellular telephones, or the like, that are capable of displaying the force, position, and/or motion information (e.g., displaying the information on an electronic display, printing the information as a hard copy, or the like). The wireless transmitter 136 may communicate with the electronic devices 138 using various types of wireless communications, such as near field communication (NFC), Bluetooth, Wi-Fi, ZigBee, cellular communication (e.g., GSM, CDMA), or the like.

Alternatively, the sensor assembly 104 could lack a wireless transmitter, and the processor 132 could operably communicate with the electronic devices 138 via a physical connection (e.g., cabling). As another alternative, the IMU 134 could include a wireless transmitter, and the IMU 134 could thereby transmit force, position, and/or motion information to the electronic devices 138.

Still referring to FIGS. 1 and 3, in some embodiments the sensor assembly 104 further includes a power supply 140 (e.g., a battery). The power supply 140 may provide electrical power to one or more of the other components of the sensor assembly 104, such as the processor 132.

Articles of handwear according to embodiments of the present disclosure may also be used in other environments (that is, non-medical environments) that would benefit from information regarding normal forces and shear forces applied by the hand of a wearer to an object. For example, articles of handwear according to embodiments of the present disclosure could be used during professional sports training, with human/machine interfaces, or other environments where manual dexterous skill is used and normal and shear force information could be used to monitor, verify, and/or improve performance of the wearer.

The present disclosure, in various aspects, embodiments, and configurations, includes components, methods, processes, systems and/or apparatus substantially as depicted and described herein, including various aspects, embodiments, configurations, sub-combinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, e.g., for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments, and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An article of handwear for grasping a medical device in a medical environment, the article of handwear comprising:
   a base adapted to be worn by a hand of a wearer;
   a sensor assembly carried by the base, the sensor assembly adapted to sense a force applied by the hand of the wearer, via the article of handwear, to the medical device, and the sensor assembly adapted to send a signal comprising information regarding a total force of the force sensed by the sensor assembly and a first component of the force sensed by the sensor assembly; and
   a processor in operable communication with the sensor assembly, the processor adapted to receive the signal and determine at least one shear component of the force sensed by the sensor assembly by using the first component and the total force.

2. The article of handwear of claim 1, wherein the sensor assembly comprises a force sensor adapted to sense the force applied by the hand of the wearer, via the article of handwear, to the medical device, and the force sensor comprises a carbon nanotube film.

3. The article of handwear of claim 1, wherein the sensor assembly comprises a force sensor adapted to sense the force applied by the hand of the wearer, via the article of handwear, to the medical device, and the force sensor comprises:
   an elastic carbon nanotube substrate adapted to sense the force applied by the hand of the wearer, via the article of handwear, to the medical device; and
   a plurality of elongated carbon nanotube members carried by the carbon nanotube substrate, the plurality of elongated carbon nanotube members being adapted to sense the force applied by the hand of the wearer, via the article of handwear, to the medical device.

4. The article of handwear of claim 3, wherein the plurality of elongated carbon nanotube members sense the total force and the carbon nanotube substrate senses the first component.

5. The article of handwear of claim 3, wherein the plurality of elongated carbon nanotube members are arranged in a grid.

6. The article of handwear of claim 1, wherein the sensor assembly comprises a force sensor adapted to sense the force applied by the hand of the wearer, via the article of handwear, to the medical device, and the base comprises:
   a palm side adapted to engage the palm of the hand of the wearer;
   wherein the force sensor is carried by the palm side.

7. The article of handwear of claim 6, wherein the base further comprises a plurality of finger portions, wherein the force sensor is a first force sensor, further comprising a second force sensor adapted to sense the force applied by the hand of the wearer, via the article of handwear, to the medical device, wherein the palm side carries the first force sensor, and one of the plurality of finger portions carries the second force sensor.

8. The article of handwear of claim 1, further comprising a wireless transmitter adapted to receive information regarding the at least one shear component and wirelessly transmit the information regarding the at least one shear component to an electronic device.

9. The article of handwear of claim 1, the sensor assembly further comprising an inertial measurement unit carried by the base, the inertial measurement unit adapted to determine a spatial position of the article of handwear and provide information regarding the spatial position of the article of handwear.

10. The article of handwear of claim 9, further comprising a wireless transmitter adapted to receive the information regarding the spatial position of the article of handwear from the inertial measurement unit and wirelessly transmit the information regarding the spatial position of the article of handwear to an electronic device.

11. An article of handwear for grasping a medical device in a medical environment, the article of handwear comprising:
    a glove adapted to be worn by a hand of a wearer;
    a plurality of force sensors carried by the glove, each of the plurality of force sensors adapted to sense a force applied by the hand of the wearer, via the article of handwear, to the medical device, each of the plurality of force sensors adapted to send a signal indicative of the force, and each of the plurality of force sensors comprising:
       a substrate of carbon-nanotube-doped elastomer adapted to sense the force; and
       a plurality of elongated carbon nanotube members carried by the substrate of carbon-nanotube-doped elastomer, the plurality of elongated carbon nanotube members adapted to sense the force.

12. The article of handwear of claim 11, wherein the glove comprises:
    a palm/opisthenar portion adapted to engage the palm of the hand of the wearer, the palm/opisthenar portion carrying a first force sensor of the plurality of force sensors; and
    a plurality of finger portions adapted to receive the fingers of the hand of the wearer, one of the plurality of finger portions carrying a second force sensor of the plurality of force sensors.

13. The article of handwear of claim 11, wherein the signal comprises information regarding a total force of the force sensed by the plurality of elongated carbon nanotube members and a normal component of the force sensed by the substrate of carbon-nanotube-doped elastomer, and further comprising a processor adapted to determine at least one shear component by subtracting the normal component from the total force.

14. The article of handwear of claim 13, further comprising an inertial measurement unit carried by the glove, the inertial measurement unit adapted to determine a spatial position of the article of handwear and provide information regarding the spatial position of the article of handwear.

15. The article of handwear of claim 14, further comprising a wireless transmitter adapted to receive information regarding the at least one shear component and the information regarding the spatial position of the article of handwear and wirelessly transmit the information regarding the at least one shear component and the information regarding the spatial position of the article of handwear to an electronic device.

16. The article of handwear of claim 11, wherein the plurality of elongated carbon nanotube members are arranged in a grid.

17. A system for determining forces transmitted from a hand of a medical practitioner to a medical device in a medical environment, the system comprising:
    a glove adapted to be worn by a hand of a wearer;
    a plurality of force sensors carried by the glove, each of the plurality of force sensors adapted to sense a force applied by the hand of the wearer, via the glove, to the medical device, each of the plurality of force sensors comprising:
- a substrate of carbon-nanotube-doped elastomer adapted to sense a normal component of the force applied to the medical device;
- a grid of elongated carbon nanotube members carried by the substrate of carbon-nanotube-doped elastomer, the grid of elongated carbon nanotube members adapted to sense a total force of the force applied to the medical device; and a processor in operable communication with the plurality of force sensors, the processor adapted to determine a shear component of the force applied to the medical device by subtracting the normal component from the total force.

18. The article of handwear of claim 17, wherein the processor is carried by the glove.

19. The article of handwear of claim 17, further comprising a remote electronic device carrying the processor.

* * * * *